(12) United States Patent
Honda et al.

(10) Patent No.: US 7,190,761 B1
(45) Date of Patent: Mar. 13, 2007

(54) X-RAY IMAGE RADIOGRAPHING METHOD AND RADIOGRAPHING APPARATUS

(75) Inventors: Chika Honda, Hino (JP); Akira Ishisaka, Hino (JP); Hiromu Ohara, Hino (JP)

(73) Assignee: Konica Corporation (JP)

( * ) Notice: Subject to any disclaimer, the term of this patent is extended or adjusted under 35 U.S.C. 154(b) by 0 days.

(21) Appl. No.: 09/616,608

(22) Filed: Jul. 14, 2000

(30) Foreign Application Priority Data

Jul. 16, 1999 (JP) .................................. 11/203969

(51) Int. Cl.
*G01N 23/04* (2006.01)
(52) U.S. Cl. .......................................... 378/62; 378/37
(58) Field of Classification Search ................... 378/37, 378/57, 62, 119, 121, 207
See application file for complete search history.

(56) References Cited

U.S. PATENT DOCUMENTS

| | | | | |
|---|---|---|---|---|
| 2,650,308 A | * | 8/1953 | Catlin | .................. 378/163 |
| 4,622,688 A | * | 11/1986 | Diemer et al. | ............... 378/143 |
| 4,979,198 A | * | 12/1990 | Malcolm et al. | ............. 378/102 |
| 5,209,232 A | * | 5/1993 | Levene | ......................... 378/37 |
| 5,305,365 A | * | 4/1994 | Coe | .............................. 378/37 |
| 5,802,137 A | | 9/1998 | Wilkins | ........................ 378/85 |
| 6,212,254 B1 | * | 4/2001 | Wilkins | ........................ 378/62 |

FOREIGN PATENT DOCUMENTS

| EP | 0 784 202 A2 | 7/1997 |
|---|---|---|
| WO | WO 96/31098 | 10/1996 |
| WO | WO 98/28950 | 7/1998 |

OTHER PUBLICATIONS

Wolbarst Physics of Radiology. p. 196-199, 202 220-221.*

* cited by examiner

*Primary Examiner*—Courtney Thomas
(74) *Attorney, Agent, or Firm*—Cantor Colburn LLP

(57) ABSTRACT

A X-ray image radiographing method of detecting a X-ray image passing an object irradiated with X-ray emitted from a X-ray tube by a X-ray detector, includes a step of increasing a sharpness of an image lowered due to penumbra by enhancing an edge of the image with refraction contrast enhancement.

16 Claims, 7 Drawing Sheets

INVENTIVE EXAMPLE
BUBBLE

INVENTIVE EXAMPLE
SCREW

COMPARATIVE EXAMPLE
BUBBLE

COMPARATIVE EXAMPLE
SCREW

X-RAY IMAGE RADIOGRAPHING METHOD AND RADIOGRAPHING APPARATUS

BACKGROUND OF THE INVENTION

The present invention relates to a X-ray radiographing method and a radiographing apparatus capable of being applicable to medical service and non-destructive test, in particular, to a X-ray radiographing method and a radiographing apparatus capable of depicting a boundary of a radiographed object with high contrast.

When an object is irradiated with X-ray emitted from a X-ray source, difference in transmission amount of X-ray transmitting the object is caused by difference in atomic weight of materials constituting the radiographed object. Accordingly, an X-ray image can be formed by detecting the two dimensional distribution of the transmission amount of X-ray.

Incidentally, since X-ray is an electromagnetic wave, X-ray has a nature of a wave. Accordingly, when X-ray transmits an object, diffraction or refraction is caused by deviation in phase and the diffraction or the refraction can be detected as an image. Conventionally, a X-ray image formation by utilizing the above nature has not been conducted. However, recently, a method of radiographing a X-ray image of an object with high contrast by utilizing the above nature has been suggested. The X-ray image obtained by this method is called a phase contrast X-ray image. In this image, since the contrast at a boundary region of the object may be enhanced, the detected ability of a X-ray image can be increased. Therefore, the method is desired to be applied to medical service using X-ray and non-destructive test for industry.

Several propositions regarding the method and the apparatus for obtaining the phase contrast X-ray image have been made. However, these techniques are insufficient in the point of actual use at a working spot where an image is obtained.

For example, in an official publication of TOKKAIHEI 10-248833, a phase contrast X-ray radiographing apparatus according to a interference method employing a Mach Zehnder type interferometer by using a synchrotron radiation X-ray has been suggested. Further, in "Medical Applications of Synchrotron Radiation" (M. Ando and C. Uyamam eds., Springer-Verlag Tokyo, 1998), a lot of technical reports to apply the phase contrast X-ray image by using the synchrotron radiation X-ray to medical service are described.

These methods are conducted by using the synchrotron radiation X-ray generating apparatus. This apparatus can obtain a strong monochromic X-ray in the form of a spatial coherent parallel light. The form that X-ray is "spatial coherent" or "lateral spatial coherent" provides the characteristics that the X-ray has coherence as wave.

Here, the synchrotron radiation X-ray generating apparatus is set up recently as "SPring-8" in Akou-districts Hyogo-prefecture and also in the physical construction science research institute in a higher energy accelerator research organization. However, these apparatus are too huge constructions to be utilized by private medical facilities and needs a huge amount of construction cost. Therefore, these apparatus have hardly been utilized by a private facility for medical purpose or other inspections.

Further, Wilkins reported a method of obtaining a phase contrast X-ray image from a fish or a small animal by using a micro focus X-ray source and the radiographing method for the X-ray image is described in the patent publication WO 96/31098. In this publication, Wilkins describes a X-ray image radiographing apparatus and a radiographing method by using the apparatus in which a X-ray source having a size of focal spot deemed as a spot light source such as a size of focal spot not larger than 20 μm is used in order to obtain X-ray having a high lateral spatial coherence and the distance between an object to be radiographed and a X-ray detector is set more than 0.3 m.

In the above science magazine, there is reported an experiment result in which a micro focus X-ray source having the size of focal spot of 20 μm used and a fish or a small animal is used as an object to be radiographed. In the method reported by Wilkins, since the size of focal spot of the X-ray tube is too small, X-ray is obtained by only a small radiation amount. Accordingly, it is reported that in the X-ray image radiography for fish, the radiographing time of about 2 hours was needed to obtain a X-ray image on a silver salt photographic film. From the above report, it may be difficult to widely apply the above method to a clinical site to radiograph a human body or to an inspection for a substance. On the other hand, if a size of focal spot is made larger, the penumbra is caused by the size of focal spot. Therefore, there may happen that the sharpness of an image is lowered or an unsharp image is caused.

SUMMARY OF THE INVENTION

The present invention has been conceived in view of the above problem and an object of the invention is to provide a X-ray image radiographing method capable of obtaining a widely practically usable phase contrast X-ray image and a radiographing apparatus using the method in contrast with a conventional X-ray imaging method and an apparatus for the conventional method which is lack of practical use in a working spot for medical service or non-destructive test.

In the present invention, by the following structures, the above problems can be solved and the above object can be attained.

(1) In a X-ray image radiographing method of detecting by a X-ray detector a X-ray image passing an object irradiated with X-ray emitted from a X-ray tube;

increasing a sharpness of an image lowered due to penumbra by enhancing an edge of the image with refraction contrast enhancement.

(2) In a X-ray image radiographing method using a X-ray tube having a size D of focal spot of 30 μm or more;

setting a distance R1 between the X-ray tube and an object so as to be within a range defined by the following formula:

$$R1 \geq (D-7)/200 \text{ (m)};$$

setting a distance R2 between the object and a X-ray detector so as to be not smaller than 0.15 (m); and radiographing the object.

(3) In the X-ray image radiographing method of (2), the distance R1 between the X-ray tube and the object is set to be within a range defined by the following formula:

$$10 > R1 \geq (D-7)/200 \text{ (m)}$$

(4) In the X-ray image radiographing method of (2) or (3), the size of focal spot is 30 μm to 1000 μm.

(5) In the X-ray image radiographing method of one of (2) to (4), the size of focal spot is 50 μm to 500 μm.

(6) In the X-ray image radiographing method of one of (2) to (5), energy of X-ray in a line spectrum is 10 keV to 60 keV.

(7) In the X-ray image radiographing method of one of (2) to (6), an anode of the X-ray tube contains molybdenum or rhodium.

(8) In the X-ray image radiographing method of one of (2) to (6), a screen/film system having an image contrast $\overline{G}$ of 1.5 to 3.6 is used.

(8') In the X-ray image radiographing method of one of (2) to (6), a screen/film system having an image contrast $\overline{G}$ of 1.5 to 4.0 is used.

(9) In the X-ray image radiographing method of one of (2) to (8), a digital X-ray detector having a size of a pixel of 1 μm to 200 μm is used.

(10) In the X-ray image radiographing method of (9), an enhanced boundary portion of the object is detected from the obtained image data and a width of the boundary portion and/or image contrast is further enhanced.

(11) In the X-ray image radiographing method of one of (2) to (10), the object is a human body or a specimen sampled from a human body.

(12) In the X-ray image radiographing method of one of (2) to (11), the object is a breast or a specimen sampled from the breast.

(13) A X-ray image radiographing apparatus, comprising:
 a X-ray tube having a size of focal spot of 30 μm or more;
 a fixing means for fixing a position of an object to be radiographed; and
 a X-ray detector to detect a X-ray image passing through the object;
wherein the fixing means is able to set such that a distance R1 between the X-ray tube and the position of the object fixed by the fixing means so as to be within a range defined by the following formula:

$$R1 \geq (D-7)/200 \text{ (m); and}$$

a distance R2 between the position of the object fixed by the fixing means and a X-ray detector so as to be not smaller than 0.15 (m).

(14) In the X-ray image radiographing apparatus of (13), the distance R1 between the X-ray tube and the position of the object fixed by the fixing means is settable within a range defined by the following formula:

$$10 > R1 \geq (D-7)/200 \text{ (m)}$$

(15) In the X-ray image radiographing apparatus of (13) or (14), the size of focal spot is 30 μm to 1000 μm.

(16) In the X-ray image radiographing apparatus of one of (13) to (15), the size of focal spot is 50 μm to 500 μm.

(17) In the X-ray image radiographing apparatus of one of (13) to (16), energy of X-ray in a line spectrum is 10 keV to 60 keV.

(18) In the X-ray image radiographing apparatus of one of (13) to (17), an anode of the X-ray tube contains molybdenum or rhodium.

(19) In the X-ray image radiographing apparatus of one of (13) to (18), a screen/film system having an image contrast $\overline{G}$ of 1.5 to 3.6 is used.

(19') In the X-ray image radiographing apparatus of one of (13) to (18), a screen/film system having an image contrast $\overline{G}$ of 1.5 to 4.0 is used.

(20) In the X-ray image radiographing apparatus of one of (13) to (19), a digital X-ray detector having a size of a pixel of 1 μm to 200 μm is used.

(21) In the X-ray image radiographing apparatus of (20), an enhanced boundary portion of the object is detected from the obtained image data and a width of the boundary portion and/or image contrast is further enhanced.

(22) In the X-ray image radiographing apparatus of one of (13) to (21), the object is a human body or a specimen sampled from a human body.

(23) in the X-ray image radiographing apparatus of one of (13) to (22), the object is a breast or a specimen sampled from the breast.

DETAILED DESCRIPTION OF THE RPEFERRED EMBODIMENT

Figure 1:
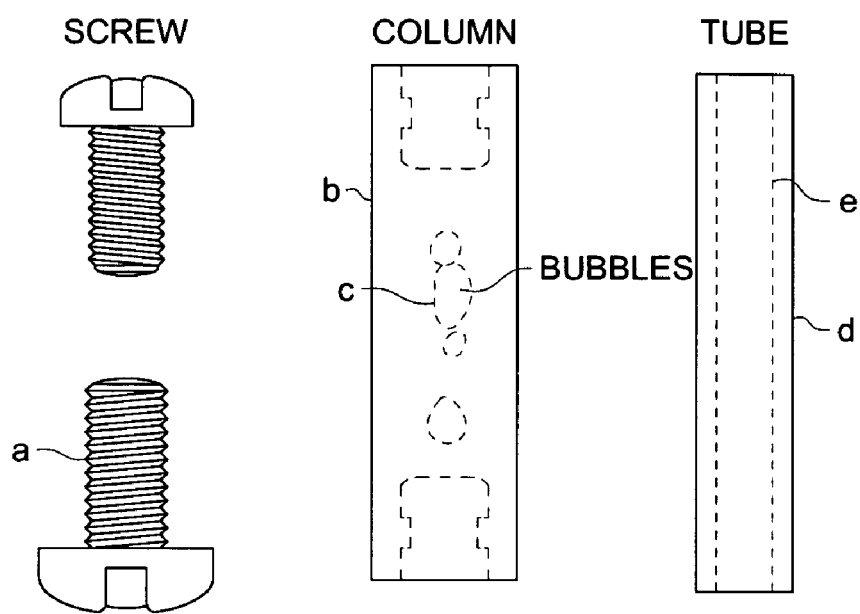
FIG. 1 is an illustration showing a X-ray image radiographing apparatus.

The X-ray image radiographing method and the apparatus for the method in the present invention is illustrated conceptually as shown in FIG. 1.

As structural elements, there are provided fixing means 4 to determine the positions of a X-ray tube 1 and an object to be photographed and to fix them at the respective positions and a X-ray detector 3. The distance between the X-ray tube 1 and the object 2 is represented as R1 and the distance between the object and the X-ray detector 3 is represented as R2. Incidentally, although the fixing means is provided at the X-ray detector-side of the object in FIG. 1, it may be provided at the X-ray tube-side.

According to the invention, a high contrast image can be obtained by using a X-ray tube usable generally at a medical facility without using the synchrotron in the huge facility or the micro focus X-ray source whose X-ray amount is very small. It may be preferable that a rotating anode type X-ray tube is used as the X-ray tube in this embodiment. In this rotating anode type X-ray tube, electron beams emitted from a cathode collides onto the anode, thereby generating X-rays. Thus generated X-rays are incoherent (non-coherence), are not parallel X-rays and are divergent rays. If the electron beams continuously collide the fixed portion of the anode, the anode may be damaged due to heat generation. Therefore, in the X-ray tube used generally, the anode is rotated so as to avoid the lower in life span of the anode. On the working condition that electron beams collide onto a portion on the plane surface of the anode having a predetermined size and thus generated X-rays are emitted from the portion on the anode to the object, the portion viewed back from the emitting direction is called a focus point. The size of the focus point is represented as D and the size D of the focus point can be measured from a half-width in the intensity distribution of the radiation source. Although the focus point may be shaped in various forms, the size of focus point is a length of a side in the case of a square, a length of a shorter side in the case of a rectangle or a polygon and a diameter in the case of a circle.

The X-ray detector creates image information by converting the X-ray energy into the other energy. As the X-ray detector, a detector employing a screen (intensifying screen)/film, a system employing a stimulable phosphor, a system employing a combination of X-ray phosphor and CCD or CMOS, or a system employing a combination of X-ray phosphor or X-ray photoconductor and TFT may be used. In the present invention, it may be preferable to use a X-ray tube having a size of a focal spot of 30 μm or more.

Figure 3:
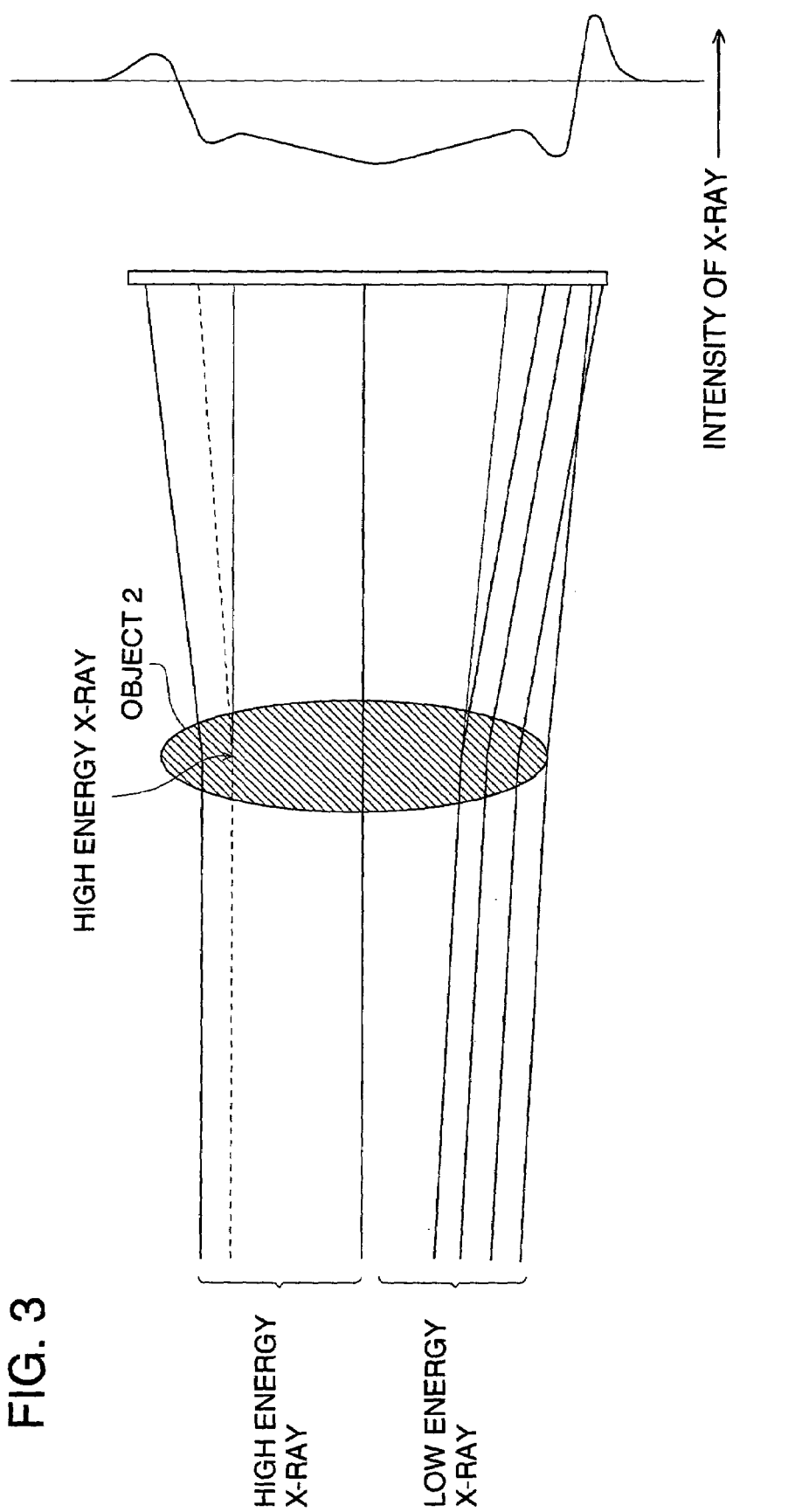
FIG. 3 is an illustration showing a process that an edge-enhanced image is obtained from a high energy X-ray.

In the X-ray image photography, as shown in FIG. 3, edge-enhanced image due to refraction of X-ray (refraction contrast enhancement) can be obtained. As depicted at the lower section in FIG. 3, when X-rays pass through a substance, since the X-rays refract such that the density of X-rays at an inner side of the boundary of the substance becomes sparse. On the contrary, at the outside of the substance, since X-rays not passing through the substance are superimposed, the density of X-rays becomes abundant. By this refraction, the edge of the image corresponding to the boundary of the substance can be enhanced, thereby obtaining an edge enhanced image. This is a phenomena caused by the difference in refractive index for X-ray between the substance and air.

Further, not only the edge enhancement at the boundary between the object and air as shown in FIG. 3 with which a principle of this enhancement is explained, but also the similar effect can be obtained at the boundary section between sections differing in refractive index in the substance. In the present invention, the boundary section of an object to be radiographed can be defined as the boundary section between materials differing in refractive index.

Figure 7:
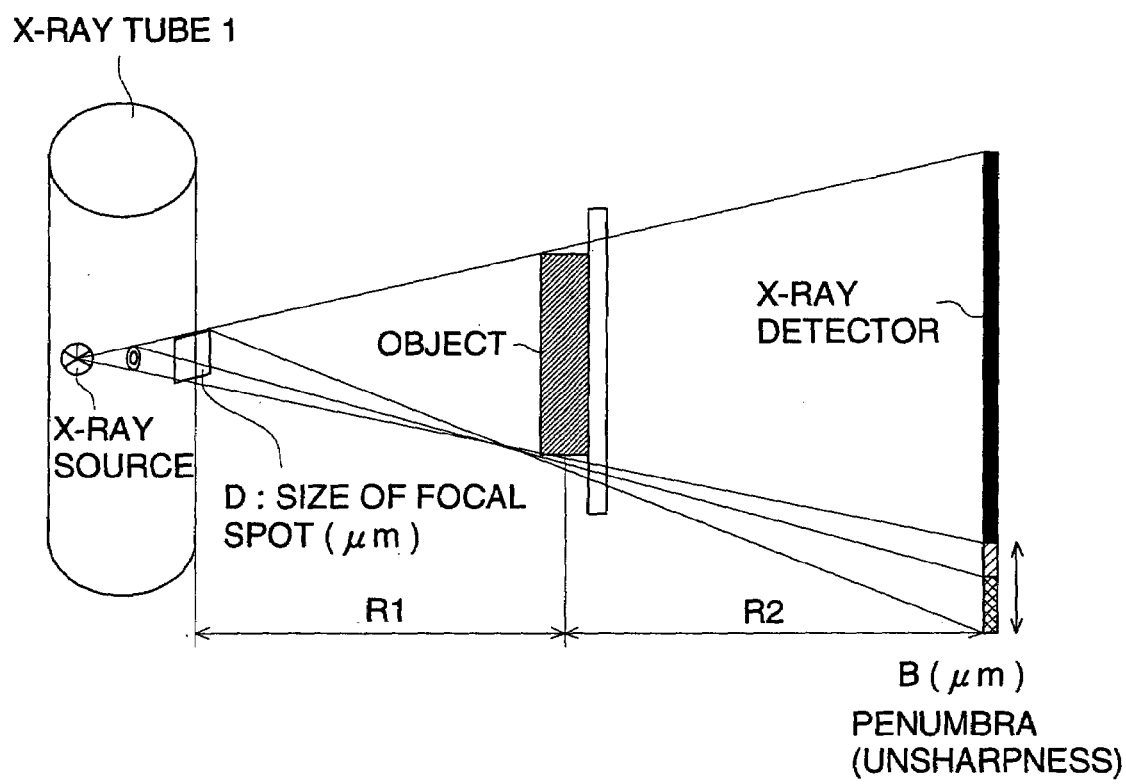
FIG. 7 is an illustration showing penumbra caused by a size of focal spot of a X-ray source.

On the other hand, as shown in FIG. 7, the penumbra caused by the size D of focal spot, in other word, blur takes place in an image. The sharpness of the image is lowered due to the penumbra. The present invention is to recover or enhance the lowered sharpness. For the recovering or the enhancing, the present invention uses the refraction contrast enhancement caused by the refraction of X-ray. Here, the penumbra is a phenomenon in which a certain point on the object to be radiographed is detected as an image having a certain size as shown as B in the example in FIG. 7 due to the size of focal spot. In other word, the penumbra means blur so called. Therefore, the influence of the penumbra may raise a problem in the case that a X-ray tube having a size of focal spot of a finite size is used for the synchrotron from which emitted X-rays are parallel rays or for the micro focus X-ray source deemed as a point-shaped light source.

In the present invention, the effect of the edge enhancement can be obtained without using the synchrotron radiator which needs a large scale apparatus or a X-ray light source whose X-ray focal spot size is small to be deemed as a point-shaped light source.

As a result of diligent study, as a condition where an edge-enhanced image can be obtained with a sensitive region and a size of an apparatus in the practical range, when the X-ray focal spot size D is 30 μm or more, it is found to be preferable that the region satisfies the formula: $R1 \geq (D-7)/200$ (m), where R1 is a distance between the X-ray tube 1 and the object 2 and a distance R2 between the object 2 and the X-ray detector 3.

If R1 is smaller than the distance represented by the formula: $R1 \geq (D-7)/200$ (m), it may be difficult to obtain br to recognize an edge-enhanced image. On the other hand, when R1 is getting larger, since the intensity of X-ray becomes weaker or a more wide space is needed, it may be preferable that R1 is not larger than 10 (m).

Incidentally, for the purpose of removing scattered rays of X-rays from the object which lowers the sharpness of the X-ray image, it has been conventionally conducted to use a X-ray grid. However, the X-ray grid reduces an amount of X-ray arriving the X-ray detector 3. Therefore, it may be preferable not to use the X-ray grid in order to use the amount of X-ray effectively.

In the present invention, by the structure that the distance R2 between the object and the X-ray detector 3 is made longer than 0.15 (m), it makes it easy to conduct removing the scattered rays and to recognize the edge enhancement.

In the present invention, if R2 is larger than 0.15 (M), the radiophotography becomes an enlarging radiophotography having a magnification ratio (MR=(R1+R2)/R1). Here, the starting point of R1 is a position at the focal spot which is clearly indicated on the X-ray tube 1 obtainable at a usual market and the ending point is at a point of the center line of the object 2 fixed by the fixing means 4. The starting point of R2 is at the position of the center line of the object 2 and the ending point is the uppermost surface on the plane surface receiving X-ray in the X-ray detector 3. In Table 1, the lower limit values of R1 which are obtained from the formula: $R1 \geq (D-7)/200$ (m) and correspond to the sizes of focal spot D are indicated.

TABLE 1

LOWER LIMIT VALUES OF DISTANCE R1
BETWEEN X-RAY SOURCE AND OBJECT

| D (μm) | R1 (m) |
|---|---|
| 30 | 0.12 |
| 50 | 0.22 |
| 100 | 0.47 |
| 200 | 0.99 |
| 500 | 2.47 |
| 800 | 3.97 |
| 1000 | 4.97 |

In order to shorten a radiographing time, it may be preferable that an amount of X-ray per unit time is greater. On the other hand, if the size of focal spot is made larger, it may be necessary to make R1 larger in order to obtain edge-enhanced X-ray image.

Generally, facilities for medical service or inspection has a limitation for a spatial margin. Therefore, in the present invention, it may be preferable that R1 is not larger than 5 (m). Further, in order to make the edge enhancement stronger, it may be preferable that R1 is not smaller than 0.7 (m). Here, if R2 is made a distance longer than 0.15 (m), a radiographed X-ray image is obtained under an enlarging radiophotography. At this times the magnification ratio is represented by (R1+R2)/R1. If the distance R1 between the X-ray source and the object is set smaller, the magnification ratio becomes larger. In the case that a screen/film is used as the X-ray detector at the time of radiographing a X-ray image, an image having a magnification ratio corresponding to R1 and R2 is obtained and the magnification ratio can be set optionally in accordance with the purpose.

Figure 2:
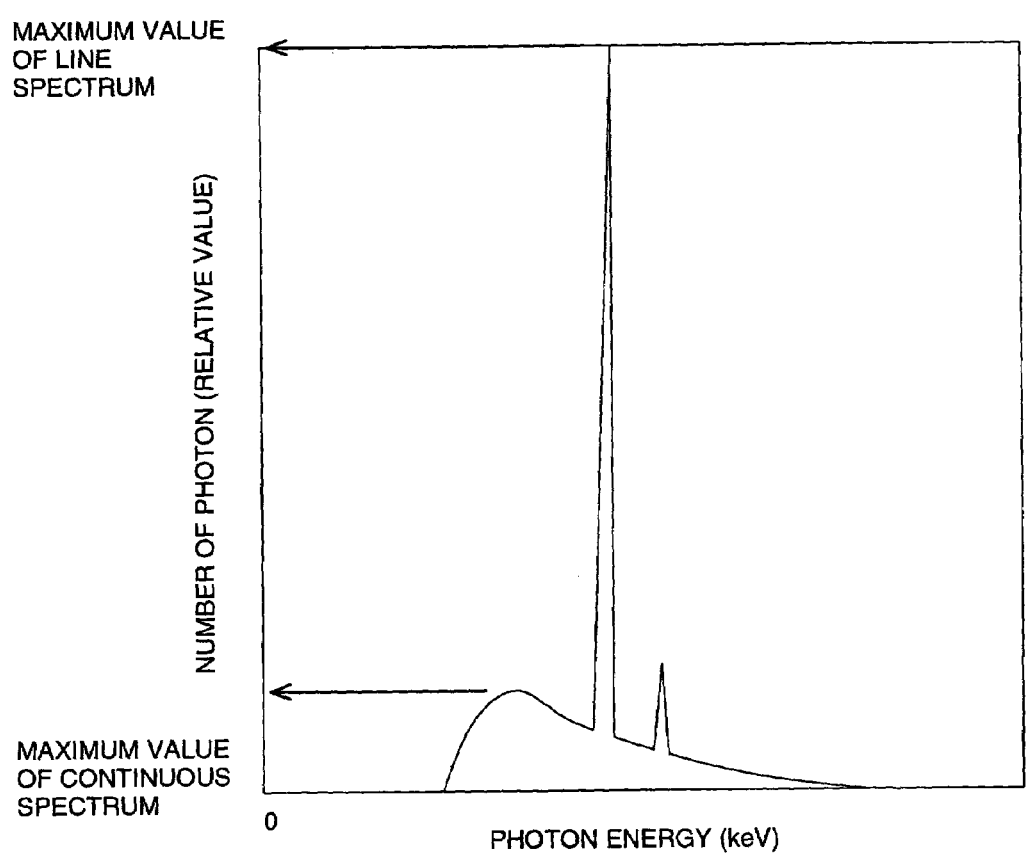
FIG. 2 is a diagram explaining line spectrum.

It may be preferable that X-ray used in the present invention is made substantially a line spectrum. Now, the definition "X-ray is made substantially a line spectrum" means that the maximum number of photon in the continuous spectrum is not larger than 50% of the maximum number of photon in the line spectrum in the X-ray output spectrum including line spectrum and continuous spectrum (FIG. 2). The refractive index of X-ray changes depending on the energy of X-ray. As shown in the left-half potion of FIG. 3, the higher the energy of X-ray is, the lower the refractive index of X-ray becomes. Therefore, in the case that the energy distribution of X-ray is wider, since the width of the refractive index also becomes wider, the refraction contrast becomes lower. On the other hand, if the line spectrum is used, since the width of the energy of X-ray is small, a more clear edge-enhanced image can be obtained (FIG. 3). Here, as the means for increasing the amount of X-ray arriving at the X-ray detector, it may be possible to make the distance between the X-ray source and the X-ray detector shorter, also it may be possible to make the size of focus point larger. However, as shown in FIG. 1, reversely, it is necessary to make R1 larger. Therefore, when in the medical facility, there is a spatial limitation for the building, if the size of focal spot is made smaller as far as possible, R1 can be made smaller.

Accordingly, it may be preferable to make the size of focal spot to be not larger than 1000 μm. Further, it may more preferable to make the size of focal spot of the X-ray tube 1 within a range of 50 μn to 500 μm.

Generally, a range of the energy of X-ray used for the X-ray image radiography for medical image diagnosis is 10 kev to 150 keV. On the other hand, in non-destructive test, a high energy X-ray higher than 200 keV is used. When the energy of X-ray is high, the refractive index of the X-ray becomes low. Therefore, in the case that the radiography is conducted in the general medical facility having a limited space, it may be preferable to use the X-ray having a low energy. However, if the energy of X-ray is too low, the X-ray loses its specific characteristic to transmit the substance. Therefore, from the view of practical use, as described in items (6) and (17), it may be preferable that the energy of X-ray in the line spectrum is in the rage of 10 keV to 60 keV.

As described in items (7) and (18), it may be preferable that an anode of the X-ray tube contains molybdenum or rhodium. When the anode of the X-ray tube is made of molybdenum, the X-ray tube has the strong line spectrum light emission in the vicinity of 17 keV. When the anode of the X-ray tube is made of rhodium, the X-ray tube has the strong line spectrum light emission in the vicinity of 20 keV. The X-rays in this region are preferable, because the X-rays in this region are superior at depicting a flesh section in a human body, so called, soft tissue.

As the X-ray detector 1, it may be preferable to use a screen/film system comprising an intensifying screen composed of a phosphor such as calcium tungstate and gadolinium oxysulfide and a silver salt photographic film in which an emulsion layer containing silver halide particles is coated on one side or both sides of a support of polyester film. In this case, it may be preferable to use a screen/film system having an image contrast $\overline{G}$ of 1.5 to 4.0.

In the present invention, as described in Items (8) and (19), it may be more preferable to use a screen/filter system having an image contrast $\overline{G}$ of 1.5 to 3.6. Even in the region having a low screen contrast of about 1.5, a photographing allowability (latitude) becomes broader and an image having a good sharpness can be obtained.

Further, in the system having a $\overline{G}$ being in the vicinity of 3.6, an image having a more good sharpness can be obtained without deteriorating the graininess of the image. Here, in the present invention, $\overline{G}$ is defined as an inclination of the line a point at the fog of +0.25 and a point at the fog of +2.0 on a performance curve obtained after exposing and developing.

Here, the performance curve is a curve drawn by indicating the logarithm of amount of exposure on the axis of abscissas and the photographic density on the axis of ordinates so as to show a relationship between an amount of light irradiated to the film and an image density. Further, the fog is a density obtained by developing a non-exposed portion.

In the present invention, the contrast at boundary surfaces differing refractive index for X-ray in the object can be enhanced. Therefore, a X-ray image provided with the enhanced image contrast can be obtained without increasing the contrast of the screen/film system. That is, $\overline{G}$ is 2.0 to 3.0. It may be preferable to use a screen system having a relatively low contrast.

As stated above, even if a screen/film system belonging in a relatively low contrast region is used, according to the invention, a sufficiently high contrast image can be obtained and the graininess of the image is not roughened. Further, for example, in the radiography for a breast, since the latitude is made broader, a periphery of the breast can be depicted so as to show its fine section. Also, since the sharpness is enhanced, a breast radiograph having a high detecting ability for a calcified portion in the breast. As the main factors influencing $\overline{G}$ of the screen/film system, the film and the developing process may be listed. In the case of the film, the composition, the size and the distribution of the silver halide particles constituting the emulsion layer, the additive such as fog inhibitor and an amount of silver halide particles used for coating. The kind and the amount of spectral sensitizing dye (spectral sensitizer) influences it. A silver halide photo-sensitive material used in the invention, for example, is described in the publication "Revised version of Basic of Photographic Technology—Vol. Silver Salt Photograph—" (compiled by Japanese Photographic Institute and published by Corona-Sha 1998). Further, by changing developing temperature or developing time period in the developing process, $\overline{G}$ can be changed. However, basically, it may be preferable to conduct the developing process in accordance with the developing condition specified by the film maker.

Recently, in the X-ray detector, the digital X-ray image radiographing system, so called, has been used in place of the traditional screen/film system. For example, the computed radiography (CR) using a stimulable phosphor, the system using the X-ray phosphor and CCD or CMOS in combination, or a plane type X-ray image detector using a X-ray phosphor or a X-ray photoconductor and TTF in combination. In the present invention, these X-ray image detector can be also used.

In these digital X-ray image radiographing system, a X-ray image information is read out by dividing a two dimensional plane surface. The length of a side of a square or the diameter of a circle each having a read-out minimum area is called the size of a pixel. For example, the size of a pixel corresponds to a pitch at the time of reading stimulated light emission in CR, the minimum reading diameter of CCD or CMOS, the reading diameter of silicon optical diode or the minimum size of pixel collecting generated charge in a X-ray photoconductor layer in FPD.

Here, the actual measurement value on the edge enhanced density increasing portion or density decreasing portion on the image formed by a silver salt photographic film is of several μm order. Therefore, it may be preferable that the minimum size of pixel of CCD or CMOS is not larger than several μm. Reversely, if it is larger than 200 μm, the sharpness of the read image is lowered or deteriorated.

In the present invention, as described in Items (9) or (20), it may be preferable to use the digital X-ray detector of which the size of pixel to detect a X-ray image is not larger than 200 μm and not smaller than 1 μm.

In the present invention, in the case that a stimulable phosphor is used in order to detect X-ray, reading out image signals is conducted by a laser exposure scanning. It may be preferable that the minimum size of pixel is equal to the diameter of a laser spot. Although the diameter is preferably not smaller than 1 μm, when the minimum size of pixel is small, since the reading speed becomes lowered, it may be preferable that the diameter is not smaller than 20 μm. On the other hand, if it is larger than 200 μm, since the tendency that the sharpness of the read image itself is deteriorated is noticed, it may be preferable that the diameter is not larger than 200 μm. Also, in the case that a flat type image detector is used, the minimum size of pixel is preferably not smaller than 1 μm, more preferably 20 μm and it may be preferable that the minimum size of pixel is preferably not larger than 200 μm.

In the present invention, in the case that a digital X-ray detector is used, the size of an output image for observation can be determined freely. In the present invention, although an image is projected on the X-ray detector with a magnification ratio corresponding to R2 and R1, if a digital X-ray image detector is used, it may be possible to indicated an image in actual size by reducing it at the time of observation.

In the present invention, as described in Items (10) and (21), an enhanced boundary section of the radiographed object is detected from the obtained image data, the width and/or the image contrast at the boundary section is further enhanced.

Figure 4:
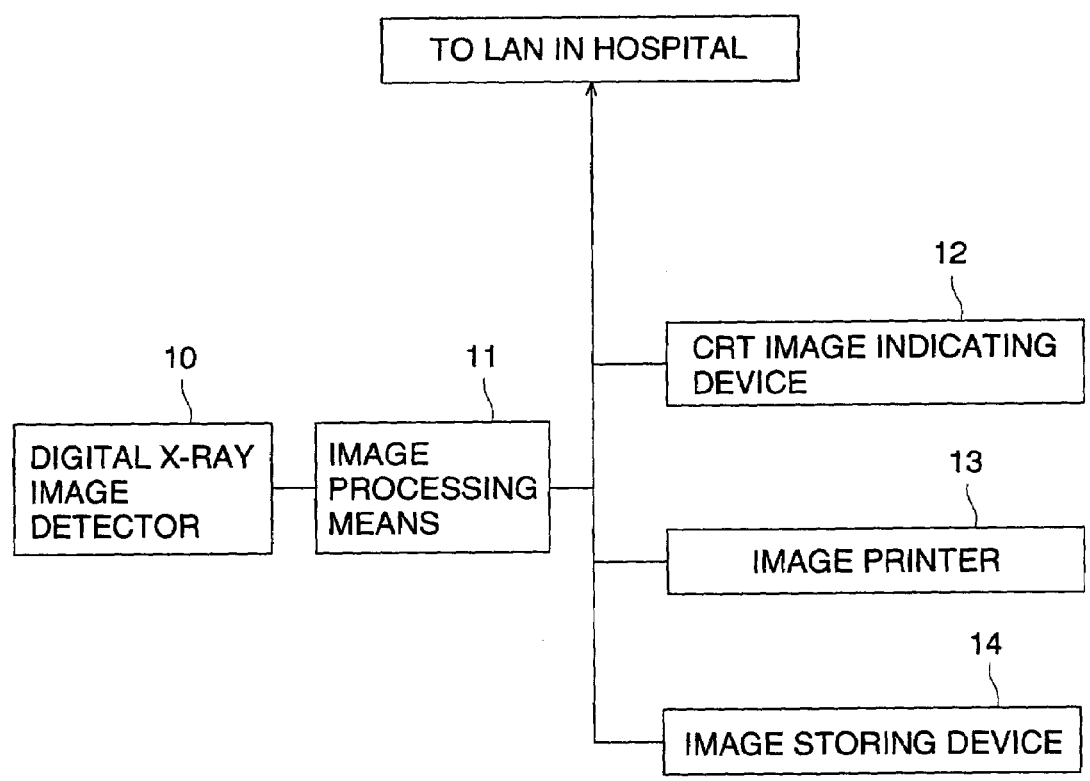
FIG. 4 is an outlined structural view of an X-ray image radiographing apparatus.
Figure 5:
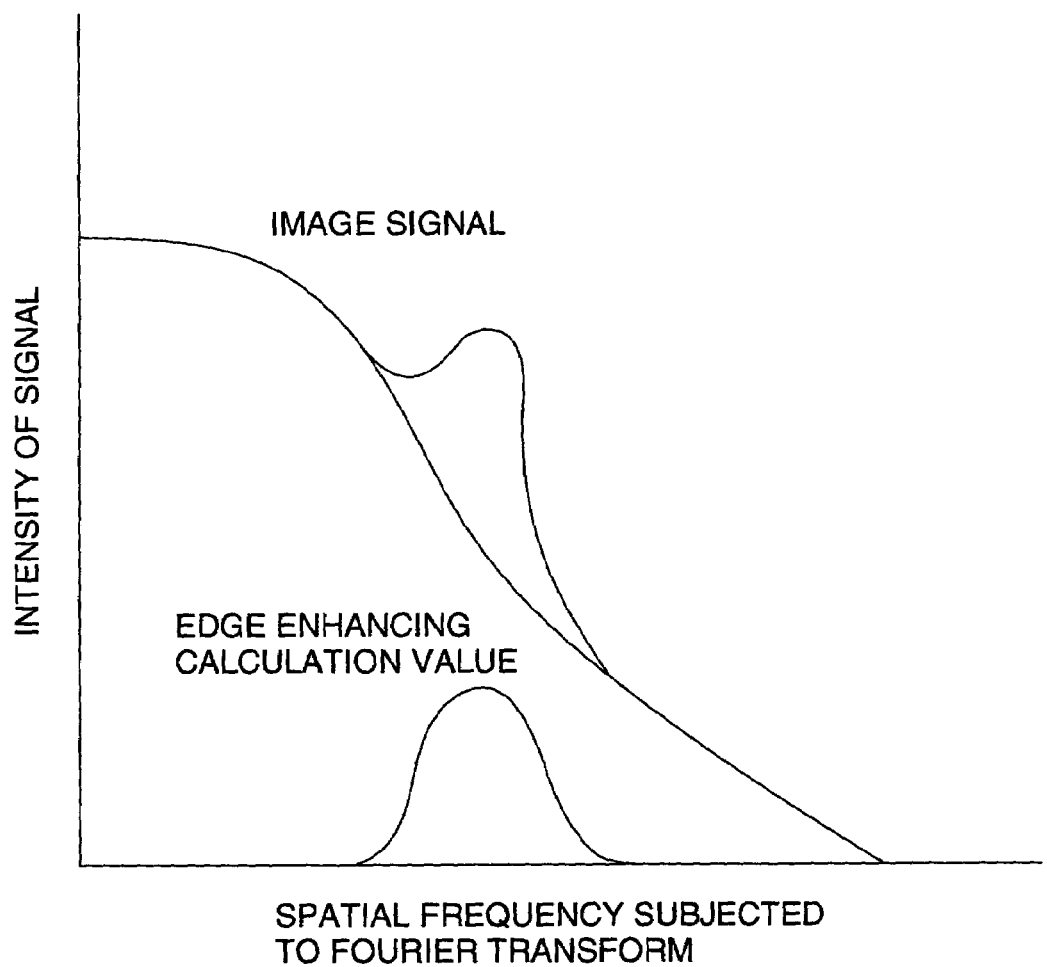
FIG. 5 is a diagram showing a relationship between an intensity of a signal and a spatial frequency subjected to Fourier transform.

The X-ray image radiographing apparatus of the present invention is shown in FIGS. 4 and 5. FIG. 4 is a block diagram showing an outlined structure of the X-ray image radiographing apparatus. FIG. 5 is a diagram showing a relationship between the intensity of signal and the spatial frequency subjected to Fourier transform.

The X-ray image radiographing apparatus comprises a digital X-ray image detector 10, an image processing means 11, CRT image displaying apparatus 12, an image printer 13 and an image storing apparatus 14. The image processing apparatus 11 conducts image processing for a digital X-ray image obtained by the digital X-ray image detector 10.

The image processing by the image processing means 11 can be attained as follows.

Edge sections peculiar to refraction contrast are detected by, for example, a pixel mask, and the contrast of the sections are expanded.

Alternatively, as shown in FIG. 5, a pattern of estimated refraction contrast is subjected to Fourier transform so as to obtain the frequency components as edge enhancement calculation values. Thereafter, in the frequency processing for the entire image, the frequency components corresponding to the refraction contrast are enhanced. The digital X-ray image subjected to the image processing in the above method are outputted to the CRT image displaying apparatus 12 and the image printer 13, and stored in the image recording apparatus 14 or transmitted to LAN in a hospital.

The present invention can be preferably applied to medical service. That is, as described in Items (11) and (22), the object is a human body or a specimen sampled from a human body.

Further, in the present invention, as described in Items (12) and (23), the object is a breast or a specimen sampled from the breast.

Conventionally, in Mammography radiography, a X-ray tube having a molybdenum anode is used and the radiography is conducted with a magnification ratio of 1 to 2 times. The size of focal spot is preferably 100 μm to 600 μm. The distance between the X-ray tube and a X-ray detector is preferably not smaller than 0.3 m, even in an enlarging radiography, not exceeds 0.6 m. This conventional radiographing condition does not fully satisfy the radiographing condition of the present invention and could not obtain the boundary contrast enhanced image of the object.

Hereinafter, the embodiment of the present invention will be explained more in detail on the basis of Examples.

EXAMPLE 1

BY using A rotating anode type X-ray tube "Rotor-anode DRX-B1146B-Mo", line X-rays were obtained through 0.03 mm molybdenum filter on the condition that tube voltage was 28 kVp and the size of focal spot was 100 μm. Line spectrum was at about 17 keV. At this time, the maximum value of the number of the continuous spectrum photon is 7% of the maximum value of the number of line spectrum photon, as shown in FIG. 2.

The X-ray tube is arranged to be horizontal so as to make the proceeding direction of the X-ray parallel to the ground and the object is placed with the distance R1, and then the X-ray detector is placed with the distance R2 from the object.

A film for mammography CMH manufactured by Konica and a one side intensifying screen M-200 are combined so as to construct the X-ray detector. After X-ray radiographing, the film was processed for 90 seconds on the temperature of 34° C. by the automatic processing machine SRX-502. The contrast of this screen/film system measured preliminary by the distance method was $\overline{G}$=3.2.

Figure 6:
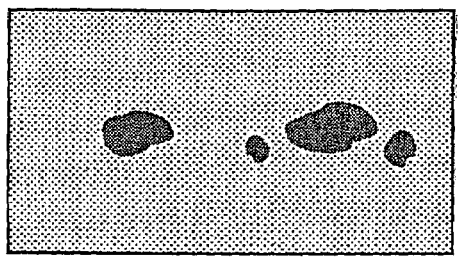
FIGS. 6(a) and 6(b) are sectional views showing a image of an inventive example and FIGS. 6(c) and 6(d) are sectional views showing a image of a comparative example.
Figure 6:
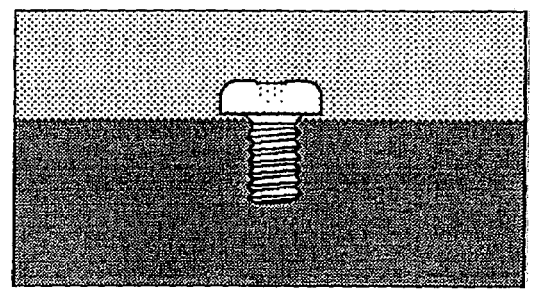
Figure 6:
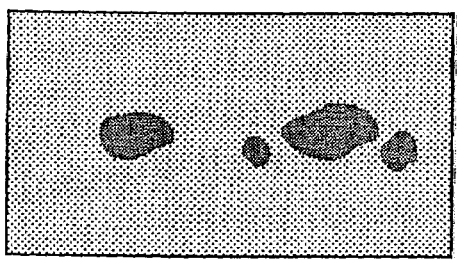
Figure 6:
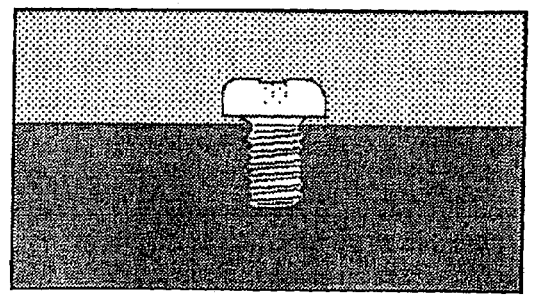

A cylinder-shaped resin which has a diameter of 1 cm and contains bubbles therein and the tip of a circular cone-shaped pipette which is made of resin and having a diameter of 1 cm were used as objects and the radiographing was conducted for them. The radiographing condition of the present invention was that the radiographing was conducted for 0.5 seconds with R1=1 m, R2=0.5 m, 10 mA so as to obtain a X-ray image with the magnification ratio of 1.5 times, (FIGS. 6(a) and 6(b)). FIGS. 6(a) and 6(b) are drawings prepared by imitating the photograph of the image of the inventive example submitted with a petition to submit a material. The image of the comparative example at the time of R1=0.6 m and R2=0 is shown in FIGS. 6(c) and 6(d). FIGS. 6(c) and 6(d) are also drawings prepared by imitating the photograph of the image of the comparative example submitted with a petition to submit a material. In order to make the comparison easier with the image of the inventive example, the magnification of the image shown in FIGS. 6(c) and 6(d) are the same as that of the image shown in FIGS. 6(a) and 6(b).

In the drawing (Photograph 1) in FIG. 6(a), the periphery edge of the bubbles in the cylinder-shaped resin are recognized as being white. In the tip of a circular cone-shaped pipette, the periphery at the inside of curved surface is enhanced to be white. Whether the edge is enhance to be white or to be black is determined depending on which one of refractive indexes of the two materials is larger. In the present invention, in any case of white or black, the edge enhancement can be obtained.

EXAMPLE 2

The distances R1 and R2 in Example 1 were varied and the extent of the edge enhancement was visually checked.

The film CMH produced by Konica Corp. and the intensifying screen M100 produced by Konica Corp. were used. After radiographing, the developing processing was conducted by Konica-manufactured SRX-503 at the temperature of 34° C. After, the developing processing, the samples were hanged up in the light box of fluorescent light (viewing lantern) and were judged with the naked eyes. The results are shown in Table 2.

Results were classified into five steps: 5 in the case that edge enhancement was very clearly observed, 4 in the case that edge enhancement was clearly observed, 3 in the case that edge enhancement was very easily observed, 2 in the case that edge enhancement was very slightly observed, and 1 in the case that edge enhancement was not clearly observed. Incidentally, when the size of focal spot was made 600 μm with the distance of R1=0.5 m, R2=0.5 m, edge enhancement was not observed. (In this case, from the formula: R1≧(D−7)/200 (m), it is necessary to make R1 more than 3 m).

According to the formula: R1≧(D−7)/200 (m), when the size of focal spot is 100 μm, R1 is that R1≧0.47. From Table 2, the present invention which satisfied the formula: R1≧(D−7)/200 (m) was evaluated so highly.

EXAMPLE 3

The X-ray image radiography was conducted in accordance with Example 1. The results were indicated in Table 3. As a object, 156 type mammographic phantom manufactured by RMI Corp. in compliance with ACR Standard is used. The film CMH produced by Konica Corp. was used. AS the intensifying screen, M100, M200 having a large amount of light emission, and a fluorescence intensifying screen for back of SRO500 having a more large amount of light emission, manufactured by Konica Corp. respectively, were appropriately used.

The phantom used in this example is prepared with the consideration for a breast of a human which is compressed in the thickness of about 4.5 cm. In the phantom, six units of nylon fibers imitating the fiber organization, five units of oxidized aluminum speck imitating a group of micro calcified substances, and six units of nylon fibers imitating a tumor are stuffed in. the numbers summed up the numbers of observed substances becomes a score. As the actual use, the total number of 4 points in the fiber, 3 points in the speck and 3 points in the tumor is the lowest score in the full score of 16 points. Here, the back densities are adjusted to be the same level of about 1.3.

TABLE 3

| No. | Screen | R1 (m) | R2 (m) | Fiber | Speck | Tumo | Total | Magnification ratio | Amount of radiation | Remarks |
|---|---|---|---|---|---|---|---|---|---|---|
| 1 | M100 | 0.6 | 0 | 5 | 4 | 3 | 12 | 1 | 526 mR | Com. |
| 2 | same above | 0.5 | 0.25 | 5 | 5 | 4 | 14 | 1.5 | 1716 mR | Inv. |
| 3 | same above | 1.0 | 0.5 | 6 | 5 | 5 | 16 | 1.5 | 3010 mR | Inv. |
| 4 | M200 | 0.6 | 0 | 4 | 4 | 4 | 12 | 1 | 263 mR | Com. |
| 5 | same above | 0.5 | 0.25 | 5 | 5 | 4 | 14 | 1.5 | 772 mR | Inv. |
| 6 | same above | 0.6 | 0.3 | 5 | 5 | 4 | 14 | 1.5 | 789 mR | Inv. |
| 7 | same above | 1.0 | 0.5 | 6 | 5 | 4 | 15 | 1.5 | 1118 mR | Inv. |
| 8 | SRO500 | 0.6 | 0 | 4 | 3 | 3 | 10 | 1 | 395 mR | Com. |
| 9 | same above | 1.0 | 0.5 | 6 | 5 | 4 | 15 | 1.5 | 688 mR | Inv. |

TABLE 2

| No. | R1 (m) | R2 (m) | Evaluation | Magnification ratio | Remarks |
|---|---|---|---|---|---|
| 1 | 0.5 | 0.25 | 3 | 1.5 | Inv. |
| 2 | 0.5 | 0.5 | 3 | 2 | Inv. |
| 3 | 1.0 | 0.5 | 4 | 1.5 | Inv. |
| 4 | 1.3 | 0.5 | 4 | 1.38 | Inv. |
| 5 | 1.5 | 0.3 | 4 | 1.20 | Inv. |
| 6 | 3 | 1.4 | 5 | 1.47 | Inv. |
| 7 | 0.3 | 0.5 | 1 | 3 | Comp. |
| 8 | 0.4 | 0.2 | 1 | 1.5 | Comp. |
| 9 | 1.50 | 0.1 | 1 | 1.07 | Comp. |
| 10 | 1.50 | 0 | 1 | 1.0 | Comp. |

In the present invention, in comparison with the comparative example, the detecting ability is increased. The amount of irradiation is the value representing how much amount of X-rays was the object irradiated with. 1R (roentgen) is an amount of X-ray to form a pair of ions of $2.1 \times 10^9$ pieces in the air of 1 cm$^3$ (0° C., 1 atmospheric pressure). Incidentally, it may be preferable that the amount of irradiation does not exceed 1000 mR from the view of the object exposed to X-ray. By increasing the system sensitivity by using the intensifying screen having a large amount of light emission, the improvement in the detecting ability in the actually usable region.

EXAMPLE 4

By using the film New CM produced by Konica Cop. Having $\bar{G}$ of 2.7, the experiment similar to that in Example 1 was conducted. In this example, the screen/film system was not used as the X-ray detector. Instead of it, the plate coated with a stimulable phosphor prepared on trial basis by Konica Corp. was used. After radiographing with X-ray, image information was read by irradiating the plate with laser on pitch of 87.5 μm. The read-out image signals are printed on a silver salt film by using the laser imager Li7 manufactured by Konica Ccrp and the developing process for the film was conducted by SRX-502. The size of the printed image was made equal to the actual size of the object and the printed image was observed. Thus obtained evaluation results are indicated in Table 4.

The evaluation standard is the same as that in Example 2, an intermediate delicate point between standard ranks is represented by, for example, 2–3. Further, the obtained edge sections of the image was subjected to an enhancement processing as shown in FIG. 5, in Item of Evaluation, the rank indicated in ( ) were obtained and in the result, the effect of the improvement was appreciated. In the image processing conducted here, edge enhancing components obtained previously by calculation was superimposed on the image signals subjected to Fourier transform so as to enhance the edge sections.

TABLE 4

| No. | R1 (m) | R2 (m) | Evaluation | Magnification ratio | Remarks |
|---|---|---|---|---|---|
| 1 | 0.5 | 0.25 | 2–3 (3) | 1 | Inv. |
| 2 | 0.5 | 0.5 | 2–3 (3) | 1 | Inv. |
| 3 | 1.0 | 0.5 | 3 (3) | 1 | Inv. |
| 4 | 1.3 | 0.5 | 3 (3–4) | 1 | Inv. |
| 5 | 1.5 | 0.3 | 4 (4) | 1 | Inv. |
| 6 | 3 | 1.4 | 4 (4–5) | 1 | Inv. |
| 7 | 0.3 | 0.5 | 1 (1–2) | 1 | Comp. |
| 8 | 0.4 | 0.2 | 1 (1–2) | 1 | Comp. |
| 9 | 1.50 | 0.1 | 1 | 1 | Comp. |
| 10 | 1.50 | 0 | 1 | 1 | Comp. |

In the above, although an example of the size of focal spot D of 100 μm was indicated in Examples 1 to 5, If D is not smaller than 30 μm, D other than 100 may achieve the above effect.

As described above, by the X-ray image radiographing method and the radiographing apparatus of for the method in the present invention, the widely practical usable phase contrast X-ray image can be obtained in comparison with the conventional phase contrast X-ray image which is lack of actual usability in the operating site for medical service and inspection.

What is claimed is:

1. An X-ray image radiographing method of radiographing an object of a breast, comprising
a sharpness enhancing step of increasing a sharpness of an image lowered due to penumbra by enhancing an edge of the image with refraction contrast enhancement;
the sharpness enhancing step comprising steps of:
using an X-ray tube having a size D of focal spot defined by the following formula:

$100 \text{ μm} \leq D \leq 600 \text{ μm}$;

setting a distance R1 between the X-ray tube and an object of a breast so as to be within a range defined by the following formula:

$(D-7)/200 \text{ m} \leq R1 \leq 5 \text{ m}$; and setting a distance R2 between the object and an X-ray detector so as to be within a range defined by the following formula:

$0.15 \text{ m} \leq R2 \leq 1.4 \text{ m}$.

2. The X-ray image radiographing method of claim 1, wherein the energy of X-ray in a line spectrum is 10 keV to 60 keV.

3. The X-ray image radiographing method of claim 1, wherein an anode of the X-ray tube contains molybdenum or rhodium.

4. The X-ray image radiographing method of claim 1, wherein a screen/film system having an image contrast $\overline{G}$ of 1.5 to 3.6 is used.

5. The X-ray image radiographing method of claim 1, wherein a screen/film system having an image contrast $\overline{G}$ of 1.5 to 4.0 is used.

6. The X-ray image radiographing method of claim 1, wherein a digital X-ray detector having a size of a pixel of 1 μm to 200 μm is used.

7. The X-ray image radiographing method of claim 6, wherein an enhanced boundary portion of the object is detected from the obtained image data and a width of the boundary portion and/or image contrast is further enhanced.

8. The X-ray image radiographing method of claim 1, wherein the distance R1 satisfies the following formula:

$0.7 \text{ m} \leq R1 \leq 5 \text{ m}$.

9. An X-ray image radiographing method of radiographing an object of a breast, comprising
a sharpness enhancing step of increasing a sharpness of an image lowered due to penumbra by enhancing an edge of the image with refraction contrast enhancement;
the sharpness enhancing step comprising steps of:
using an X-ray tube having a size D of focal spot defined by the following formula:

$100 \text{ μm} \leq D \leq 600 \text{ μm}$;

setting a distance R1 between the X-ray tube and an object of a breast so as to be within a range defined by the following formula:

$0.15 \text{ m} \leq R1 \leq 5 \text{ m}$; and setting a distance R2 between the object and an X-ray detector so as to be within a range defined by the following formula:

$0.15 \text{ m} \leq R2 \leq 1.4 \text{ m}$.

10. The X-ray image radiographing method of claim 9, wherein the energy of X-ray in a line spectrum is 10 keV to 60 keV.

11. The X-ray image radiographing method of claim 9, wherein an anode of the X-ray tube contains molybdenum or rhodium.

12. The X-ray image radiographing method of claim 9, wherein a screen/film system having an image contrast $\overline{G}$ of 1.5 to 3.6 is used.

13. The X-ray image radiographing method of claim 9, wherein a screen/film system having an image contrast $\overline{G}$ of 1.5 to 4.0 is used.

14. The X-ray image radiographing method of claim 9, wherein a digital X-ray detector having a size of a pixel of 1 μm to 200 μm is used.

15. The X-ray image radiographing method of claim 14, wherein an enhanced boundary portion of the object is detected from the obtained image data and a width of the boundary portion and/or image contrast is further enhanced.

16. The X-ray image radiographing method of claim 9, wherein the distance R1 satisfies the following formula:

$0.7 \text{ m} \leq R1 \leq 5 \text{ m}$.

* * * * *